United States Patent [19]
Whitworth

[11] Patent Number: 5,484,537
[45] Date of Patent: Jan. 16, 1996

[54] PARTICLE MANIPULATION IN AN ULTRASONIC FIELD

[75] Inventor: Glenn Whitworth, Marlboro, N.H.

[73] Assignee: Public Health Laboratory Service Board, Great Britain

[21] Appl. No.: 927,647
[22] PCT Filed: Mar. 8, 1991
[86] PCT No.: PCT/GB91/00373
§ 371 Date: Nov. 16, 1992
§ 102(e) Date: Nov. 16, 1992
[87] PCT Pub. No.: WO91/13674
PCT Pub. Date: Sep. 19, 1991

[30] Foreign Application Priority Data

Mar. 14, 1990 [GB] United Kingdom ................. 9005705

[51] Int. Cl.$^6$ ................................................ B01D 43/00
[52] U.S. Cl. ........................................ 210/748; 210/542
[58] Field of Search ........................... 55/277; 95/29; 209/1, 155; 210/748, 542

[56] References Cited

U.S. PATENT DOCUMENTS

| | | | |
|---|---|---|---|
| 4,523,682 | 6/1985 | Barmatz et al. | 209/638 |
| 4,736,815 | 4/1988 | Barmatz et al. | 181/0.5 |
| 4,743,361 | 5/1988 | Schram | 209/1 |
| 4,877,516 | 10/1989 | Schram | 210/748 |
| 4,941,135 | 7/1990 | Schram | 210/748 |
| 5,006,266 | 4/1991 | Schram | 209/155 |

FOREIGN PATENT DOCUMENTS

| | | |
|---|---|---|
| 0147032 | 10/1984 | European Pat. Off. . |
| 0292470 | 5/1988 | European Pat. Off. . |
| 836640 | 4/1952 | Germany . |
| 3218488 | 11/1983 | Germany . |
| 1012538 | 12/1965 | United Kingdom . |

OTHER PUBLICATIONS

Published WO application for PCT/GB87/00363 (Unilever Plc).
International Search Report list of references for PCT/GB91/00373 and Annex.
Jacobi, William J., "Propagation of Sound Waves along Liquid Cylinders", Journal of the Acoustical Society of America, vol. 21, No. 2 (Mar. 1949), pp. 120–127.
Peterson, Stephen et al., "Development of an Ultrasonic Blood Cell Separator", IEEE 8th Conf., 1986.
R. T. Beyer, Nonlinear Acoustics, (The Naval Ship Systems Command Dept. of the Navy, 1974) Chap. 9, pp. 309–311.
R. K. Gould and W. T. Coakley, Proc. of the 1973 Symposium on Finite Amplitude Wave Effects in Fluids, Ed. by L. Bjorno (Pergamon, Guilford, 1974), pp. 252–257.
W. T. Coakley, D. W. Bardsley, M. A. Grundy, F. Zamani, and D. J. Clarke, J. Chem. Tech. Biotechnol. 44, 1989, pp. 43–62.

*Primary Examiner*—Ivars Cintins
*Attorney, Agent, or Firm*—Wolf, Greenfield & Sacks

[57] ABSTRACT

An ultrasonic field is used to manipulate biological cells or other particles in fluid suspension. A cavity is bounded by a thin plastics wall and excitation is confined to a single acoustic mode to displace the cells radially. The resulting column of cells can be transported more easily than the radially diffuse bands produced in earlier apparatus.

23 Claims, 2 Drawing Sheets

PARTICLE MANIPULATION IN AN ULTRASONIC FIELD

This invention relates to the manipulation of particles in an ultrasonic field.

It is well known that particles whose acoustic properties differ from those of the medium in which they are suspended, may move when exposed to an acoustic standing wave to form regions of high concentration at half wavelength intervals. By the use of a plane acoustic wave, it has been shown that particles can be concentrated in bands corresponding to pressure nodes or anti-nodes. Techniques have been described for the manipulation of biological cells in this way providing—for example—the separation of blood cells from plasma. Reference is directed in this connection to:

Proc. of IEEE Eighth Annual Conference of the Engineering in Medicine and Biology Society pp. 154–156 Peterson et al "Development of an Ultrasonic Blood Cell Separator".

Acustica Vol. 56 1984 pp. 114–119 Weiser et al "Interparticle Forces on Red Cells in a Standing Wave Field".

WO85/01892

GB-A-2,166,659

WO87/07178

WO87/07421

EP-A-0 147 032

U.S. Pat. No. 4,673,512

GB-B-2,098,498

U.S. Pat. No. 4,055,491

In a typical known arrangement, bands of particles are formed along the axis of a cylindrical chamber and then by movement of the standing wave field by frequency or phase shifting, the banded particles are moved to a collection point. In a number of important applications, the speed at which the bands can be moved is considerably slower than would be wished.

It is an object of this invention to provide improved apparatus and method for the manipulation of particles in an ultrasonic field and, in an important example, to provide such method and apparatus which permits a more rapid collection of particles.

Accordingly, the present invention consists in one aspect in apparatus for the manipulation of particles in an ultrasonic field, comprising a chamber for containing the particles in fluid suspension, the chamber being at least in part defined by a cylindrical pressure-release wall such that acoustic fluid pressure is small at the fluid/wall boundary; acoustic transducer means adapted to generate an acoustic wave along the cylindrical axis through excitation of a single acoustic mode and transducer drive means, the arrangement being such that on excitation, the particles are radially displaced symmetrically of the cylindrical axis.

Preferably, the arrangement is such that on excitation, the particles are radially displaced inwardly to form a column along the cylindrical axis.

Advantageously, the acoustic transducer means is adapted to excite the lowest axially symmetric acoustic mode.

Suitably, the acoustic pressure amplitude at the fluid/wall boundary is no greater than 20% (and preferably no greater than 10%) of the amplitude on the cylindrical axis.

In one form of the invention, the cylindrical pressure-release wall is of circular cross section and the acoustic transducer means is adapted to produce an acoustic wave having a radial distribution of amplitude approximating to a Bessel function.

By the production of a single mode field, in contrast to the plane waves listed hitherto, the present invention enables the formation of an axial column of particles which, depending on the particle and field parameters, may be divided axially into bands. It is found experimentally that once particles have been formed into a column, it is generally possible to move them much more quickly in the axial direction than is the case with planar bands. It is believed that an explanation for this phenomenon is that particles concentrated in a radial column move in unison as a body with reduced viscous drag.

The radial displacement provided in the present invention may also permit radial separation of particles in accordance with particle size, density and adiabatic compressibility. It is also found that the use of a single-mode field substantially eliminates the acoustic streaming which is generated at the chamber wall if a plane-wave field is used.

In another aspect, the present invention consists in a method for the manipulation of particles in an ultrasonic field, comprising the steps of positioning the particles in fluid suspension within a cylindrical pressure-release wall such that acoustic fluid pressure is small at the fluid/wall boundary; and generating an acoustic wave along the cylindrical axis through excitation of a single acoustic mode, such that the particles are radially displaced symmetrically of the cylindrical axis.

Preferably, the particles are radially displaced inwardly to form a column along the cylindrical axis.

Advantageously, the lowest axially symmetric acoustic mode is excited.

In one form of the invention, the cylindrical pressure-release wall is of circular cross section and the acoustic wave has a radial distribution of amplitude approximating to a Bessel function.

Acoustic propagation along liquid cylinders, and in particular, the effect of boundary conditions upon propagation, has been the subject of study, and reference is directed in this connection to the Journal of the Acoustical Society of America, Volume 21, No. 2 March 1949, William J. Jacobi "Propagation of Sound Waves Along Liquid Cylinders". It is there shown that with pressure-release walls, that is to say with the boundary condition that the acoustic fluid pressure must vanish at the wall, there is no plane-wave mode of transmission. For a pressure-release wall, it is necessary for the wall thickness to be small and for the Young's modulus of the wall material to be low. It is shown by Jacobi that both the shear force per unit length of wall circumference and the power flow past the point in the wall due to flexural waves are proportional to $E\delta^3$ where E is the Young's modulus of the wall material and $\delta$ is the wall thickness. In practical terms, a pressure-release wall can be formed using very thin metal tubing with the outside of the tubing being exposed to a gas or vacuum. For a particular wall thickness, a further improvement can be achieved by the use of more elastic material such as rubber or plastic. In acoustic terms, an optimised wall material would perhaps be thin plastic membrane of thickness less than 100 µm, although care is then required to provide the required structural integrity. This could be achieved for example by an external sleeve of open cell foam. A more practicable alternative is believed to be a wall constructed of a closed-cell foam which can be of sufficient thickness to provide itself the required structural integrity or can serve as a pressure-release lining within a more rigid container. The closed cell Foam provides an effective membrane wall of very low thickness with the gas Filled cells to the outside of the membrane providing a pressure-release action.

The radius of the cylindrical wall is an important parameter. It can be shown that for a particle of density ρ greater than that of the fluid medium $\rho_o$ and adiabatic compressibility $\beta$ less than that of the fluid medium $\beta_o$, such as biological cells in water, the cylindrical diameter must be large in relation to an acoustic wave length. Preferably, the diameter is greater than five waive lengths and still more preferably greater than ten wave lengths. As will be described in more detail subsequently, the use of a cylindrical wall which is too narrow will result in particles which satisfy the quoted inequalities, moving towards the wall rather than moving to form an axial column. There is no theoretical upper limit on the tube diameter although as a practical matter, the time taken to form a column will increase with increasing tube diameter.

Since the fluid contained within a cylindrical wall of relatively large diameter will be capable of propagating a large number of acoustic modes, care must be taken in the design of the transducer to ensure that only the lowest axially symmetric mode is excited. For a cylindrical wall of circular cross section, the ideal transducer will produce a Bessel-shaped distribution of amplitudes along the radial dimension.

There exist design proposals For acoustic transducers which produce a Gaussian distribution of amplitudes along a radial dimension. Reference is directed in this connection to the Journal of the Acoustical Society of America, Volume 78, No. 6, December 1985 Gonghuan Du and M. A. Breazeale "The Ultrasonic Field of a Gaussian Transducer". A true Gaussian distribution does not of course fall to zero at a boundary, as does the desired Bessel function. Nonetheless, a transducer designed to produce a Gaussian field in an unbounded fluid will in practical terms suffice in the performance of the present invention. There is described in the Du paper an acoustic transducer in the form of a piezo ceramic disc having a disc-shaped rear electrode of a diameter D which is less than the diameter of the ceramic disc and between twice and four times the thickness T of the ceramic disc.

It has been Found by the present inventor that the use of an acoustic transducer as described with D=4 T will excite primarily the lowest-axially symmetric mode of a cylinder of fluid bounded by a pressure-release wall of diameter 1.5 D.

The behaviour of particles in apparatus according to this invention is believed to be capable of characterisation in terms of particle density and adiabatic compressibility relative to the medium. Distinctly different particle behaviour is anticipated for walls above and below a critical diameter.

For a more detailed explanation of the present invention and a description by way of example, reference is directed to the accompanying drawings in which.

Figure 1:
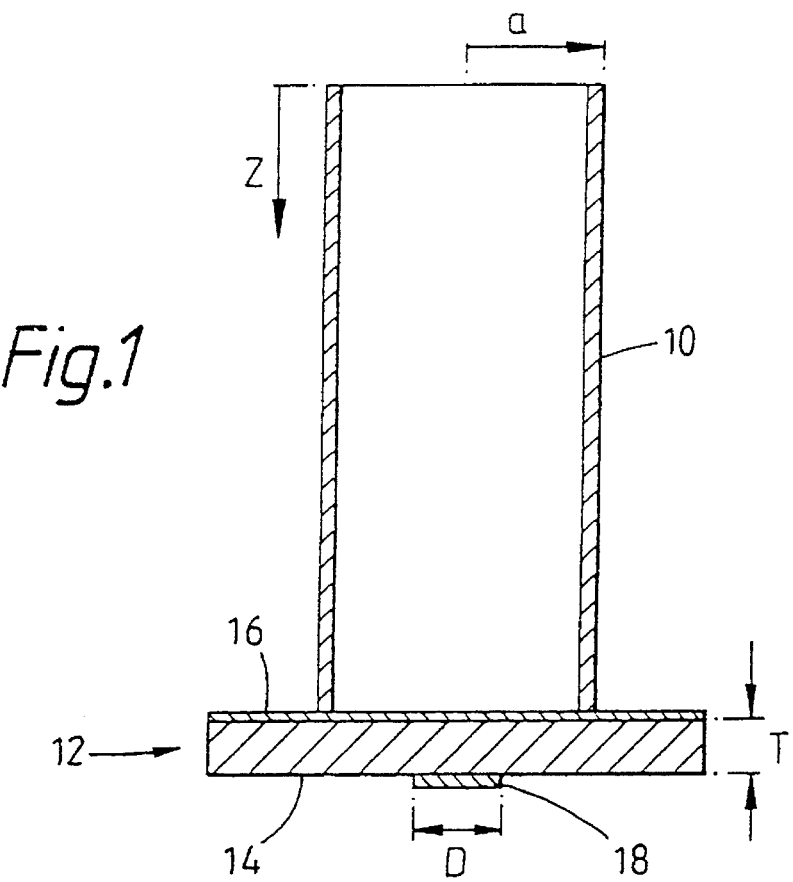
FIG. 1 is a sketch illustrating apparatus according to the present invention.

As shown in FIG. 1, apparatus according to the present invention comprises a cylindrical pressure-release wall 10 extending from an acoustic transducer 12. The transducer comprises a piezo electric disc 14 having a front electrode 16 of essentially the same diameter and a rear electrode 18 of substantially reduced diameter.

In one example, the pressure-release wall comprises a tube of circular cross section formed of cellulose acetate having the dimensions:

| Length: | 57 mm |
| Outside diameter: | 12.5 mm |
| Wall thickness: | 0.4 mm |

The tube 10 is cemented directed to the face of the transducer 12 which is air-backed. The transducer disk is formed of PZT-4 having the following parameters:—

| Diameter: | 40 mm |
| Front electrode diameter | 40 mm |
| Rear electrode diameter | 8.4 mm |
| Thickness: | 2.1 mm |
| Fundamental resonant frequency: | 1 MHz |
| Driving frequency: | 3.12 MHz (3rd harmonic) |

Figure 2:
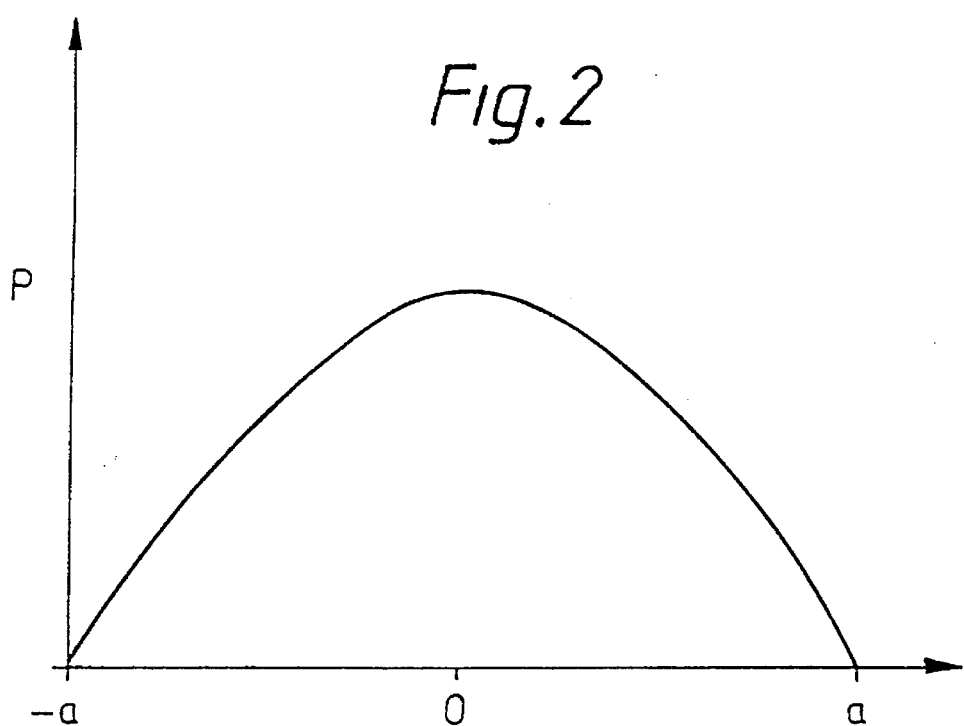
FIG. 2 is a plot showing the radial distribution of acoustic fluid pressure amplitude.

The acoustic field has the radial amplitude distribution shown in FIG. 2 and can be derived as:

$$P(r,z,t)=P_o J_o(X_{01}r/a)\sin(k_z z)\sin(wt)$$

where $$K_z=[(w/c)^2-(X_{01}/a)^2]^{1/2}=2\pi/\lambda_z.$$

Expressions can be generated for kinetic energy and potential energy in fluid medium of density $\rho_o$ and adiabatic compressibility $\beta_o$. Thus:

$$<KE>=<[\int \nabla P(r,z,t)dt]^2/2\rho_o>$$

$$<PE>=<P(r,z,t)^2>\beta_o/2.$$

In considering the movement of suspended particles of volume $V_o$, density $\rho$ and adiabatic compressibility $\beta$, it is necessary to consider acoustic radiation force, gravity and diffusion. The total potential energy U is given by:

$$U=U_g+U_a$$

where $$U_g=g(\rho-\rho_o)V_o z$$

and $$U_a=-V_o B<KE>+V_o(1-\beta/\beta_o)<PE>$$

is defined such that the acoustic irradiation force:

$$\underline{F}_a=-U_a$$

[see L. P. Gorkov, Sov. Phys Doklady 6, 773–775 (1962)].

It can be shown [see R. J. Urick, J Acoust Sec Am 20, 283–289 (1948)] that for small spherical particles, the parameter B is given by:

$$B=3(\rho-\rho_o)E/(2\rho+\rho_o)$$

where E is a viscous correction factor.

In regions where the particles are non-interacting, an equilibrium particle distribution $C(r,z)$ can be anticipated according to:

$$C(r,z)=C_o \exp[-(U-U_o)/kT]$$

Figure 3A:
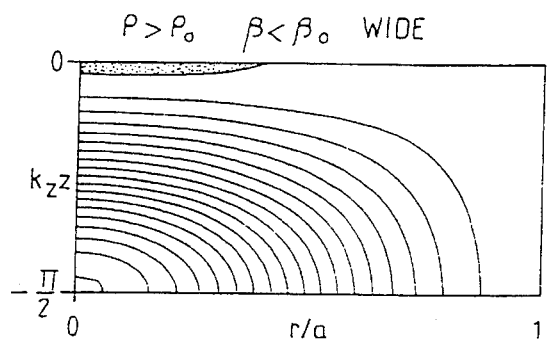
FIGS. 3(a) to 3(f) are plots showing anticipated particle concentrations for particle species characterised by density $\rho$ and adiabatic compressibility D as compared with the parameters $\rho_o$ and $\beta_o$ for the fluid medium.
Figure 3B:
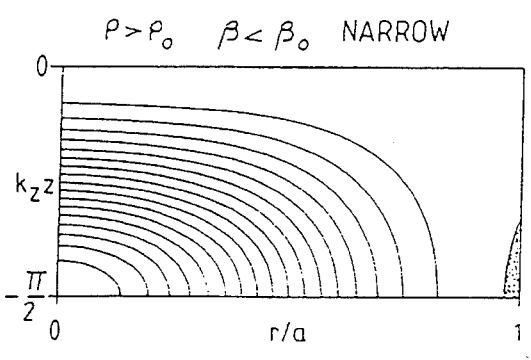

Plots showing calculated particle distributions are shown in FIGS. 3(a) to 3(f). FIG. 3(a) illustrates the case, of which biological cells in water is one example, having a particle density $\rho$ greater than that of the fluid medium $\rho_o$ and an adiabatic compressibility $\beta$ less than that of the fluid medium $\beta_o$. In this case, the diameter of the tube is greater than $10 \lambda_z$. It will be seen that particles are concentrated at the axis (r=0) with the column having an internal band structure of spacing $\lambda_z/2$. For the same particle but a narrow tube, the particles are concentrated—as shown in FIG. 3(b) on the wall of the tube (r=a). There is again an internal band structure but with a phase shift of $\lambda_z/4$ compared with the wide tube case.

Figure 3C:
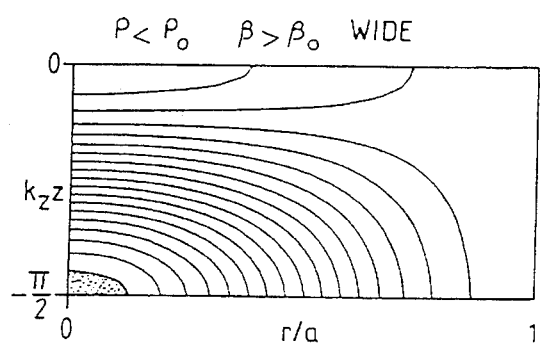
Figure 3D:
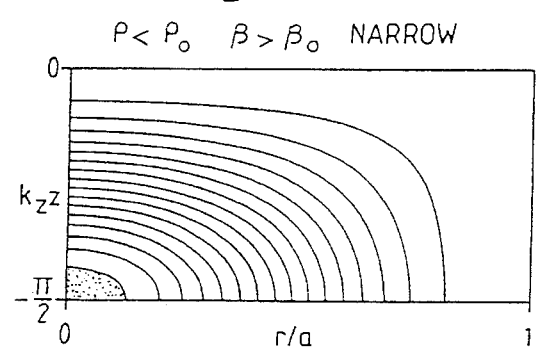

In the case of particles having a density $\rho$ less than that of a fluid density $\rho_o$ and an adiabatic compressibility D greater than that of the fluid $\beta_o$, the expected particle distributions for wide and narrow tubes are shown in FIGS. 3(c) and 3(d) respectively. In both cases, the formation of a column is expected, with an internal band structure.

Figure 3E:
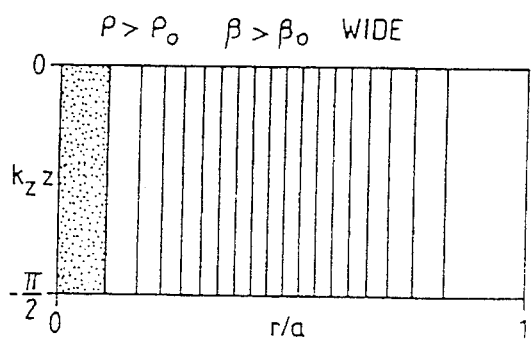
Figure 3F:
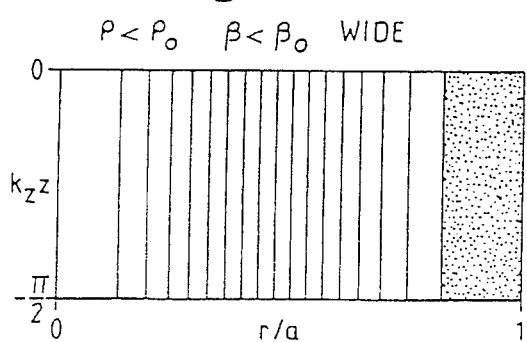

For particles having $\rho$ greater than $\rho_o$ and $\beta$ greater than $\beta_o$, the expected particle distribution for a wide tube is shown in FIG. 3(e). column is formed on the tube axis with no band structure. For the remaining case of particles having less $\rho$ than $\rho_o$ and $\beta$ less than $\beta_o$ the expected particle distribution for a wide tube is shown in FIG. 3(f). It will be seen that particles will tend to move to the wall with no column being formed.

In one experimental arrangement, a particle suspension was used of 13 µm diameter latex microspheres in water. For this suspension, $\rho$ was greater than $\rho_o$ and $\beta$ is less than $\beta_o$. With a driving voltage of 30 $V_{rms}$ representing an acoustic pressure amplitude of approximately 0.5 MPa, a central column containing most of the particles in the tube is observed to form in less than one minute. After formation of a column, the particles can be caused to move axially by a variety of techniques including frequency control. A further experiment using biological cells of approximate diameter 2 µm has again demonstrated rapid formation of a column.

It will be recognised that in the described arrangement, the liquid/air interface at the top of the chamber serves as a reflector producing a standing wave. In an alternative arrangement, the tube may be terminated with an absorber, enabling the formation of a travelling wave. It can be shown in this situation that the condition for particles to move toward the tube axis to form a column is:

$$B>(1-\beta/\beta_o)$$

This inequality is not met by the important example of biological cells in water so that the formation of standing waves will remain more important. It is believed, however, that in some applications, the use of a travelling wave field will enable separation of particles which do satisfy the inequality, from those which do not.

It is believed that the present invention will enable an improved performance to be obtained from a variety of previously proposed designs for the manipulation of particles in an ultrasonic field. The invention is accordingly not restricted to a particular manipulative technique and includes, For example, separation, harvesting, filtering, clarification of suspensions, enhancement of reaction rates, particle alignment and chromatographic like analyses. In addition, differential radial displacement as between particles characterised by values of $\rho$ and $\beta$ may provide useful manipulative techniques.

It should be understood that this invention has been described by way of examples only and a wide variety of modifications can be made without departing From the scope of the invention. Whilst a number of wall constructions have been described which will satisfy the pressure-release criterion, still others will occur to the skilled man. Similarly, alternative designs of transducer can be provided which will in the case of a cylindrical wall of circular cross section, provide an approximate Bessel shaped field and in non-circular cylinders, will act similarly to excite a single acoustic mode, preferably the lowest axially symmetric acoustic mode.

I claim:

1. Apparatus adapted for manipulation of particles in an ultrasonic field, comprising a chamber containing the particles in fluid suspension, the chamber being at least in part defined by a cylindrical pressure-release wall acoustic transducer means adapted to generate an acoustic wave, with an acoustic wavelength, along the cylindrical axis through excitation of a single acoustic mode; and transducer drive means, the arrangement being such that on excitation, the particles are radially displaced symmetrically of the cylindrical axis wherein the mean dimension of the cylindrical wall perpendicular to the cylindrical axis is greater than five times said acoustic wavelength.

2. Apparatus adapted for manipulation of particles in an ultrasonic field, comprising a chamber for containing the particles in fluid suspension, the chamber being at least in part defined by a cylindrical pressure release wall provided by a tube of plastics or rubber having a wall thickness of 1 mm or less; acoustic transducer means adapted to generate an acoustic wave along the cylindrical axis through excitation of a single acoustic mode: and transducer drive means, the arrangement being such that on excitation the particles are radially displaced symmetrically of the cylindrical axis.

3. Apparatus adapted for manipulation of particles in an ultrasonic field, comprising a chamber for containing the particles in fluid suspension, the chamber being at least in part defined by a cylindrical pressure release wall provided by a plastics membrane of wall thickness of 100 µm or less; acoustic transducer means adapted to generate an acoustic wave along the cylindrical axis through excitation of a single acoustic mode: and transducer drive means, the arrangement being such that on excitation the particles are radially displaced symmetrically of the cylindrical axis.

4. Apparatus adapted for manipulation of particles in an ultrasonic field, comprising a chamber for containing the particles in fluid suspension, the chamber being at least in part defined by a cylindrical pressure release wall provided by a cylindrical cavity within a body of closed cell foam; acoustic transducer means adapted to generate an acoustic wave along the cylindrical axis through excitation of a single acoustic mode; and transducer drive means, the arrangement being such that on excitation the particles are radially displaced symmetrically of the cylindrical axis.

5. Apparatus according to any one of claims 1–4, constructed and adapted such that on excitation, the particles are radially displaced inwardly to form a column along the cylindrical axis.

6. Apparatus according to a any one of claims 1–4, wherein the acoustic transducer means is adapted to excite the lowest axially symmetric acoustic mode.

7. Apparatus according to any one of claims 1–4, wherein the cylindrical pressure-release wall is of circular cross section and the acoustic transducer means is adapted to produce an acoustic wave having a radial distribution of amplitude approximating to a Bessel function.

8. Apparatus according to claim 1 wherein the mean dimension of the cylindrical wall perpendicular to the cylindrical axis is greater than ten times said acoustic wavelength.

9. A method for the manipulation of particles in an ultrasonic field, comprising the steps of positioning the particles in fluid suspension within a cylindrical pressure-release wall; and generating an acoustic wave along the cylindrical axis through excitation of a single acoustic mode, such that the particles are radially displaced symmetrically of the cylindrical axis.

10. A method according to claim 9, wherein the particles comprise biological cells in aqueous suspension.

11. A method according to claim 9, wherein the particles are radially displaced inwardly to form a column along the cylindrical axis.

12. A method according to claim 11, wherein the cylindrical pressure-release wall is of circular cross section and the acoustic wave has a radial distribution of amplitude approximating to a Bessel function.

13. A method according to claim 12, wherein the acoustic pressure amplitude at the fluid/wall boundary is no greater than 20% of the amplitude on the cylindrical axis.

14. A method according to claim 12, wherein said particles include at least two species of particle, the species being distinguishable one from each by particle density or particle adiabatic compressibility, such that the radial distribution of displaced particles is characteristic of the species, and wherein the step of generating an acoustic wave such that particles are radially displaced symmetrically of the cylindrical axis effects for each species of particle a different radial distribution of displacement the method comprising the further step of radially separating species of particle.

15. A method according to claim 12, wherein the acoustic pressure amplitude at the fluid/wall boundary is no greater than 10% of the amplitude on the cylindrical axis.

16. A method according to claim 11, wherein the acoustic pressure amplitude at the fluid/wall boundary is no greater than 20% of the amplitude on the cylindrical axis.

17. A method according to claim 11, wherein said particles include at least two species of particle, the species being distinguishable one from each by particle density or particle adiabatic compressibility, such that the radial distribution of displaced particles is characteristic of the species, and wherein the step of generating an acoustic wave such that particles are radially displaced symmetrically of the cylindrical axis effects for each species of particle a different radial distribution of displacement the method comprising the further step of radially separating species of particle.

18. A method according to claim 11, wherein the acoustic pressure amplitude at the fluid/wall boundary is no greater than 10% of the amplitude on the cylindrical axis.

19. A method according to claim 9, wherein the lowest axially symmetric acoustic mode is excited.

20. A method according to claim 9, wherein the cylindrical pressure-release wall is of circular cross section and the acoustic wave has a radial distribution of amplitude approximating to a Bessel function.

21. A method according to claim 9, wherein the acoustic pressure amplitude at the fluid/wall boundary is no greater than 20% of the amplitude on the cylindrical axis.

22. A method according to claim 9, wherein said particles include at least two species of particle, the species being distinguishable one from each by particle density or particle adiabatic compressibility, such that the radial distribution of displaced particles is characteristic of the species, and wherein the step of generating an acoustic wave such that particles are radially displaced symmetrically of the cylindrical axis effects for each species of particle a different radial distribution of displacement the method comprising the further step of radially separating species of particle.

23. A method according to claim 9, wherein the acoustic pressure amplitude at the fluid/wall boundary is no greater than 10% of the amplitude on the cylindrical axis.

* * * * *